United States Patent [19]
Weldon

[11] Patent Number: 5,935,141
[45] Date of Patent: Aug. 10, 1999

[54] INTERVENTIONAL CARDIOLOGY INSTRUMENT CONTROLLED FROM AN INTRACORONARY REFERENCE

[75] Inventor: Norman R. Weldon, Evergreen, Colo.

[73] Assignee: Partisan Management Group, Miami Lakes, Fla.

[21] Appl. No.: 08/960,710

[22] Filed: Oct. 30, 1997

[51] Int. Cl.$^6$ ..................................................... A61B 17/32
[52] U.S. Cl. .............................. 606/167; 606/1; 606/168; 606/170; 606/184; 606/185; 606/180; 600/434; 600/508; 600/585; 600/104; 600/117; 600/118; 600/201; 600/204
[58] Field of Search ................................. 606/1, 167, 170, 606/171, 184, 185, 180, 168; 600/434, 508, 585, 104, 117, 118, 201, 204, 205, 108

[56] References Cited

U.S. PATENT DOCUMENTS

| | | | |
|---|---|---|---|
| 4,543,090 | 9/1985 | McCoy | 604/95 |
| 4,898,577 | 2/1990 | Badger et al. | 604/53 |
| 5,188,111 | 2/1993 | Yates et al. | 128/657 |
| 5,368,564 | 11/1994 | Savage | 604/95 |
| 5,389,096 | 2/1995 | Aita et al. | 606/15 |
| 5,554,152 | 9/1996 | Aita et al. | 606/7 |

FOREIGN PATENT DOCUMENTS

WO96/35469  11/1996  WIPO ........................... A61M 25/00

OTHER PUBLICATIONS

Lee et al., Effects of laser irradiation delivered by flexible fiberoptic system on the left ventricular internal myocardium, Brief Communications, American Heart Journal, pp. 587–590 (Sep. 1993).

Sen et al., Transmyocardial acupuncture: a new approach to myocardial revascularization, J. Thorac. Cardiovasc. Surg., vol. 50, No. 2, pp. 181–189 (Aug. 1985).

Sen et al., Further studies in multiple transmyocardial acupuncture as a method of myocardial revascularization, Surgery, vol. 64, No.5, pp. 861–870 (Nov. 1968).

Jeevanandam et al., Myocardial revascularization by laser–induced channels, Surgical Forum, Cardiovascular Surgery, pp. 225–227 (Ca. 1989).

Mirhoseini et al., New concepts in revascularizatio of the myocardium, Ann. of Thoracic Surgery, vol. 45, No. 4, pp. 415–420 (Apr. 1988).

(List continued on next page.)

*Primary Examiner*—Michael Buiz
*Assistant Examiner*—(Jackie)Tan-Uyen T. Ho
*Attorney, Agent, or Firm*—David P. Gordon; David S. Jacobson; Thomas A. Gallagher

[57] ABSTRACT

A surgical instrument includes a proximal actuation handle and a flexible guiding catheter having a channeling lumen, a suction lumen, and a control lumen. The guiding catheter has a slit opening into the control lumen at its distal end. A hollow cutting member extends through the channeling lumen and is moveable distally relative to the guiding catheter with a cutting actuation mechanism. The cutting member is preferably a section of thin walled hypodermic tubing having a sharpened distal end and is provided with a first proximal connector for coupling the cutting member to a first pressure regulator. A flexible control wire extends through the control lumen and is movable distally and rotatably relative to the guiding catheter with a control actuation mechanism. The control wire is sufficiently flexible to buckle with each contraction of the heart and has a foot at its distal end located beyond the distal end of the guiding catheter and movable relative thereto by movement of the control wire. A suction conduit extends into the actuation handle and is coupled to the suction lumen of the guiding catheter. The suction conduit has a second proximal connector which is coupled to a second pressure regulator. Through manipulation of the instrument, a series of channels may be drilled in the heart wall to promote angiogenesis and reperfusion.

34 Claims, 12 Drawing Sheets

OTHER PUBLICATIONS

Ritchie et al., Myocardial imaging with thallium–201 at rest and during exercise: comparison with coronary arteriography and resting and stress electrocardiography, Circulation, vol. 56, No. 1, pp. 66–71 (Jul. 1977).

Horvath et al., Transmyocardial laser revascularization: operative techniques and clinical results at two years, J. Thorac. Cardiovasc. Surg., vol. 111, pp. 1047–1053 (May, 1996).

Mirhoseini et al., Myocardial revascularization by laser: a clinical report, Lasers in Surgery and Medicine, vol. 3, pp. 241–245 (1983).

Mirhoseini et al., Transventricular revascularization by laser, Lasers in Surgery and Medicine, vol. 2, pp. 187–198 (1982).

Kohmoto et al., Physiology, histology, and 2–week morphology of acute transmyocardial channels made with a $CO_2$ laser, Ann. Thorac. Surg., vol. 63, pp. 1275–1283 (1997).

Kim et al., Percutaneous method of laser transmyocardial revascularization, Cathet. Cardiovasc. Diagn., vol 40, pp. 223–228 (1997).

Jansen et al., Laser–tissue interaction during transmyocardial laser revascularization, Ann. Thorac. Surg., vol. 63, pp. 640–647 (1997).

Beranek, Pseudovascular tubes obscure transmyocardial revascularization, Correspondence, Ann. Thorac. Surg., vol. 63, pp. 597–598 (1997).

Annotated TMR Bibliography by PLC Medical Systems, Inc. (1997).

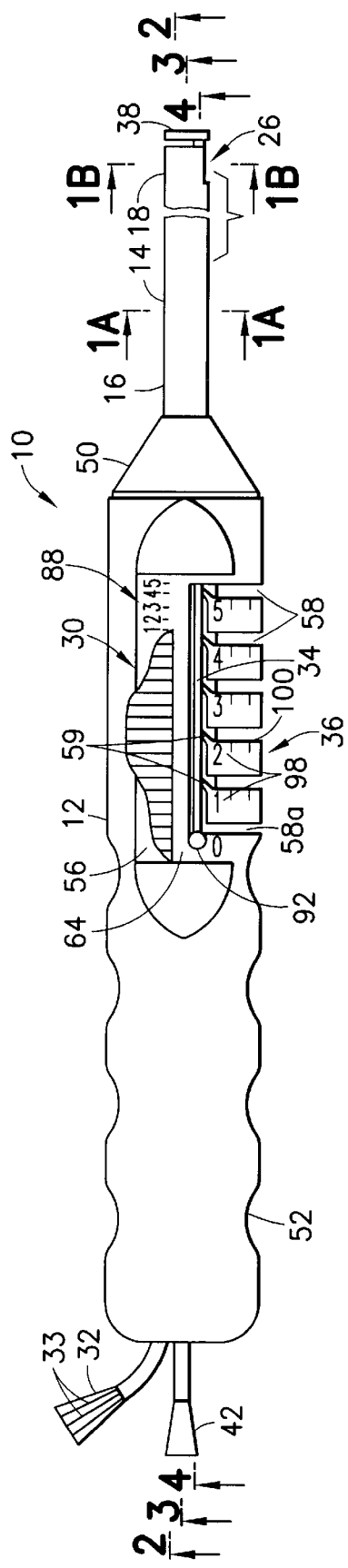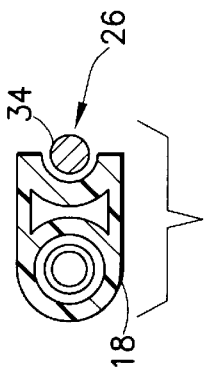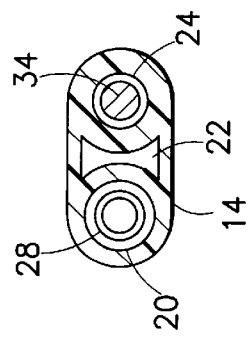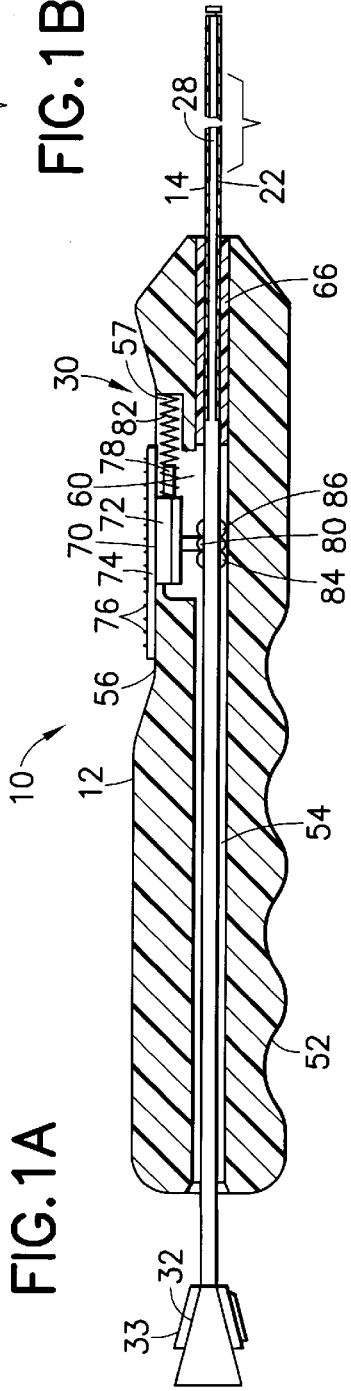

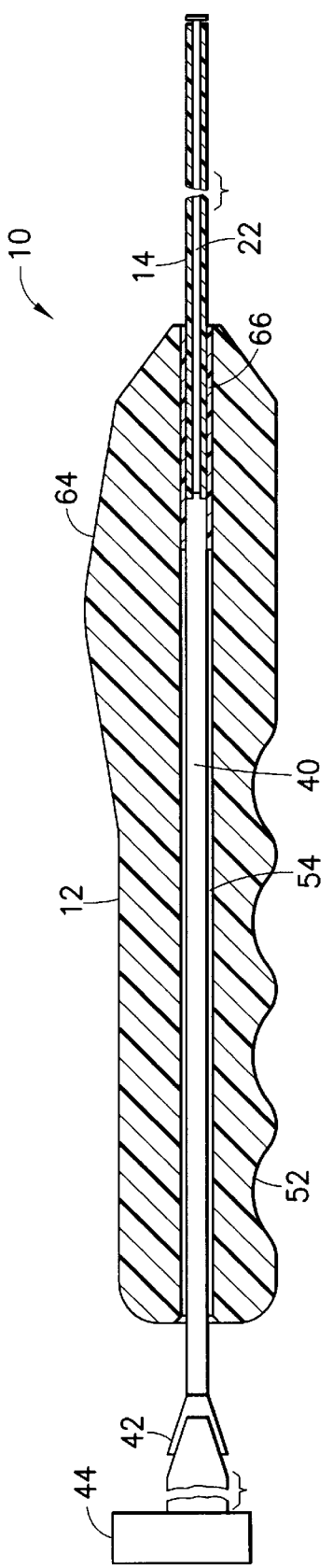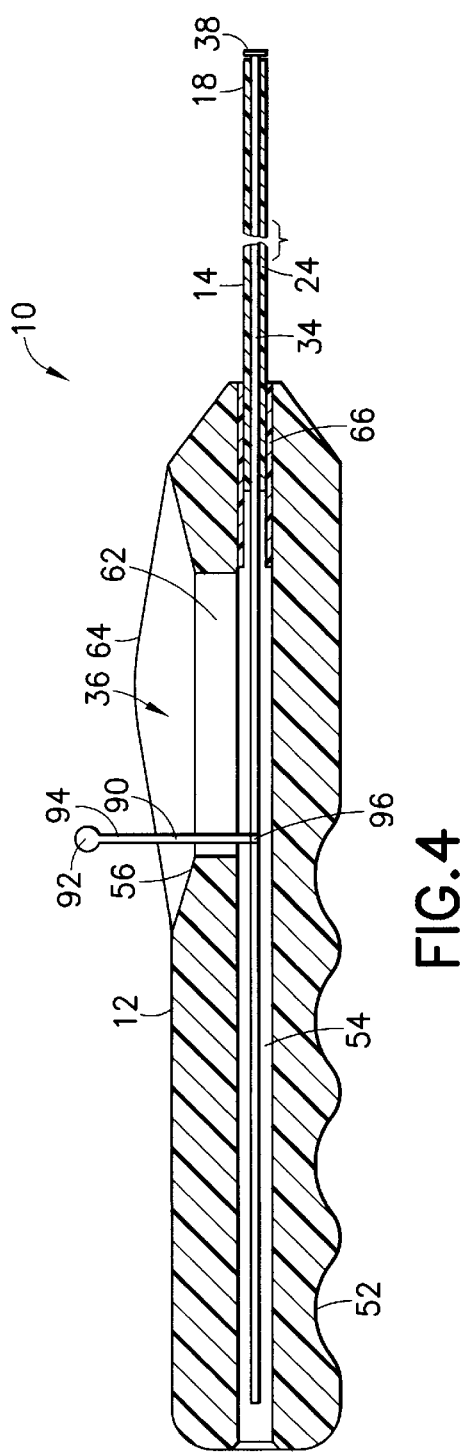

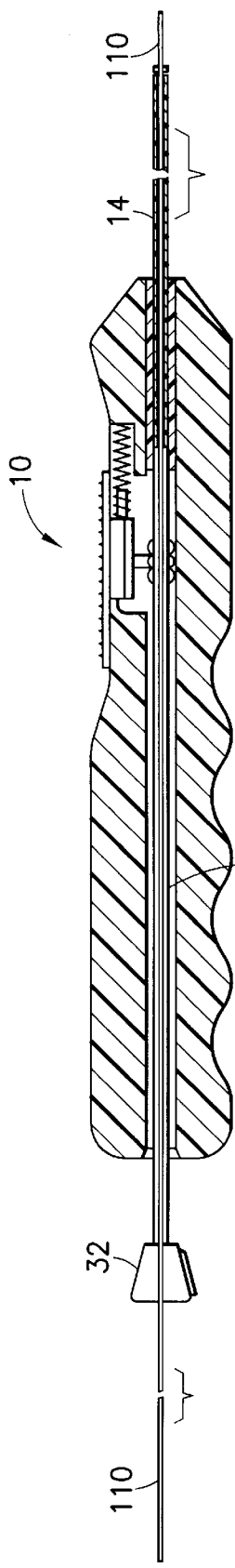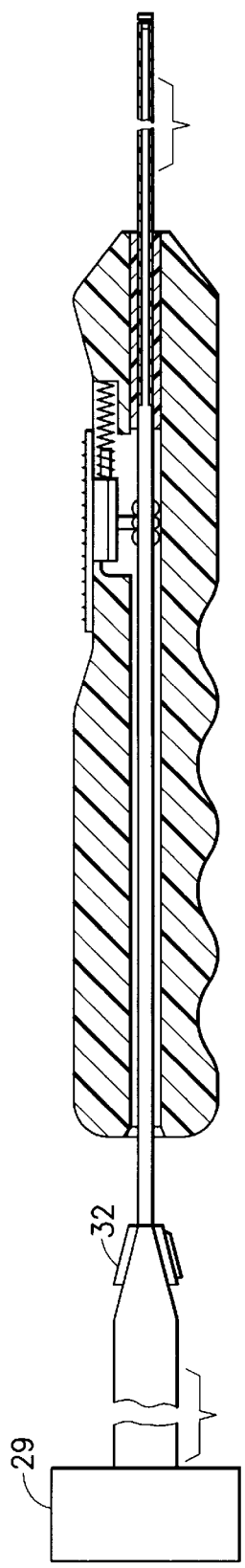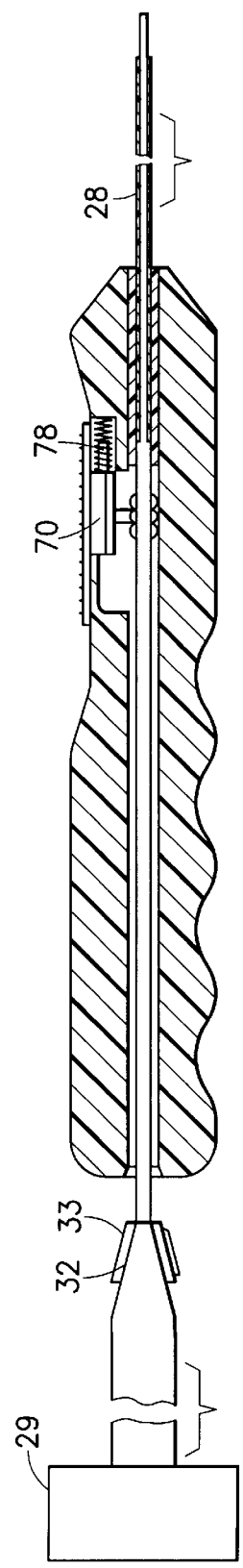

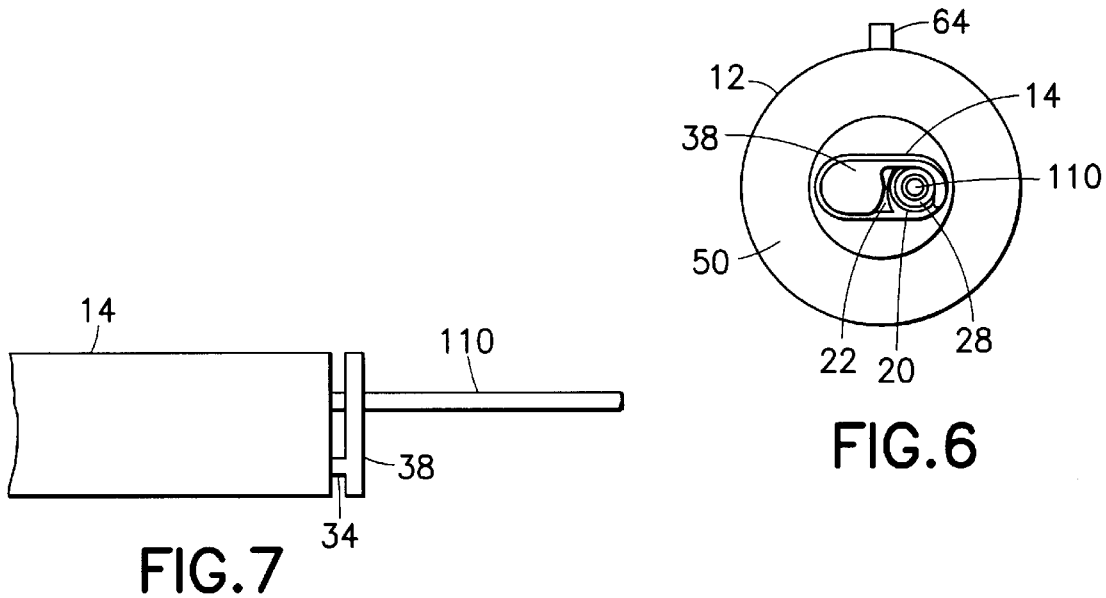
FIG.6
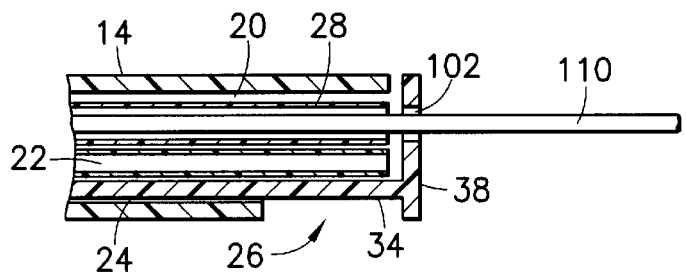
FIG.7
FIG.8
FIG.11
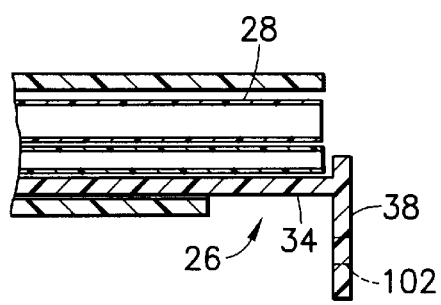
FIG.12

INTERVENTIONAL CARDIOLOGY INSTRUMENT CONTROLLED FROM AN INTRACORONARY REFERENCE

BACKGROUND OF THE INVENTION

1. Field of the Invention

This invention relates broadly to interventional cardiology. More particularly, this invention relates to instruments for performing and controlling surgical interventions within the heart.

2. State of the Art

Unlike other organs in the body, the heart is constantly beating, and therefore, constantly in motion. Contractions of the heart wall create severe difficulty in remotely directing the distal end of a laser or other surgical instrument to a desired location, as the heart wall moves with each contraction relative to the apex and distal end. Therefore, when performing less invasive surgical interventions in any chamber of the beating heart it is difficult, if not impossible, to know precisely where the distal end of the instrument is located at any one instant.

There are no known prior art surgical devices which are specifically adapted to compensate for the relative movement of the heart wall of a beating heart during interventional coronary procedures and which permit a cardiologist or surgeon to move the distal end of the instrument with respect to a known location in the beating heart, and thereby discern a relative location of the distal end of the instrument during percutaneous heart surgery.

Percutaneous transmyocardial revascularization (PMR) is becoming an accepted treatment of end stage coronary artery disease and is a procedure in which knowing the relative location of the operating end of a surgical instrument is of paramount importance. A number of companies are developing equipment and procedures to revascularize areas of the heart muscle which have been deprived of adequate circulation because of stenotic disease of the coronary arteries. All known developments use lasers to drill channels in the myocardium, and such first generation devices have shown promise.

In an earlier technology called transmyocardial revascularization (TMR) the chest of a patient was opened and a laser was used to drill multiple holes in the left ventricle under direct observation. Although effective, first generation TMR devices were successful for reasons never envisioned by their developers. TMR was intended to provide a means for permitting blood inside the ventricles to nourish the myocardium via laser drilled channels through the entire ventricular wall. In fact, the laser drilled channels clotted almost immediately. Unpredicted, however, was that new arterial channels developed in or near the laser drilled channels via angiogenesis and supplied limited quantities of oxygenated blood to the adjacent myocardium.

This recent knowledge that TMR operates via angiogenesis suggests that lasers may be suboptimal for initiating the process because of laser induced thermal damage. In addition, lasers are awkward to use in the traditional interventional cardiology procedure room and are expensive. Furthermore, the depth of the drilled channels is difficult to limit with a laser device in PMR procedures. Moreover, manipulation of the laser devices, and other potential drilling tools, is difficult and inexact.

SUMMARY OF THE INVENTION

It is therefore an object of the invention to provide a surgical instrument for use in percutaneous heart surgery.

It is another object of the invention to provide a surgical instrument having a distal end which can be moved relative to a reference point.

It is a further object of the invention to provide a surgical instrument which temporarily plants a reference means on an inner wall of the beating heart for use as a reference point.

It is an additional object of the invention to provide a surgical instrument which is accurately movable relative to a reference means.

It is also an object of the invention to provide a surgical instrument having a foot which will not provide undue stress on and puncture the heart wall.

Another object of the invention is to provide a surgical instrument which can be used to drill an array of channels in the heart wall.

Still another object of the invention is to provide a surgical instrument which can drill channels to a predetermined depth in the heart wall.

Even another object of the invention is to provide a surgical instrument for use in the heart which is easily maneuverable.

Yet another object of the invention is to provide a surgical instrument for use in the heart which is relatively less expensive than laser devices.

In accord with these objects, which will be discussed in detail below, a surgical instrument is provided which can accurately move with respect to a reference point in a chamber of a beating heart. According to the invention, the instrument generally includes a guiding catheter having a control lumen, a drilling means at the distal end of the guiding catheter, a flexible control wire extending through the control lumen of the guiding catheter and having a distal reference means, and an actuation means for moving the control wire relative to the guiding catheter. The reference means is preferably a "foot" with a relatively large surface area and which is plantable at the apex of the right ventricle or left ventricle. Once the foot is planted on the heart wall, the actuation means can be used to move the control wire relative to the guiding catheter and cause the distal end of the guiding catheter to move relative to the foot; i.e., away from the foot. In this manner, the drilling means may gradually and purposefully be moved relative to the foot to place the drilling means at desired distances from the location at which the foot is planted and thereby enable the drilling means to drill channels at various locations in the heart wall.

According to a preferred aspect of the first embodiment of the invention, the foot and guiding catheter can be moved relative to each other in a stepwise manner. According to another preferred aspect, the distal end of the guiding catheter has a slit opening entering into the control lumen. The slit opening permits lateral bowing of the control wire and provides greater mobility to the control wire.

According to a yet another preferred aspect of the invention, the guiding catheter is rotatable relative to the control wire. As a result, the drilling means can be directed through an arc to various locations on the heart wall which are at a common distance from the planted foot. Relative rotation is performed via manipulation of the actuation handle.

According to another preferred aspect of the invention, the guiding catheter has a lubricous second lumen through which the drilling means extends, and the drilling means is hollow. A guide wire is extendable through the hollow drilling means in order to guide the distal end of guiding catheter into a desired location in the heart, e.g., the left ventricle. Preferably the hollow drilling means is a very thin walled hypodermic tubing (cutting member) having a sharpened tip. Preferably the hollow cutting member is also coupled to a first pressure regulator, or vacuum source, to move cut pieces of heart tissue proximally through the cutting member and thereby clearing the cutting member at its distalmost portion to assist in subsequent "drillings".

According to yet another preferred aspect of the invention, the guiding catheter has a third suction lumen which is coupled to a second pressure regulator. When a vacuum is applied during use, the distal end of the guiding catheter at the suction lumen is held relatively stably against the heart wall of the beating heart and the drilling means is able to drill a channel into the stably held heart wall.

According to another preferred aspect of the invention, the proximal actuation handle includes means for moving the drilling means relative to the guiding catheter, a stop for limiting the distance the drilling means may be moved relative to the guiding catheter, and an indicator means for indicating the distance the drilling means has been moved relative to the distal end of the guiding catheter. In addition, means for moving the control member in a stepwise manner relative to the guiding catheter and, therefore, the reference means stepwise relative to the distal end of the guiding catheter is also provided, as is an indicator means for indicating the distance the control member has been moved relative to the guiding catheter.

With the above invention, it will be appreciated that the instrument may be used to perform surgery within the heart and especially PMR surgery. In practice, a guide wire is inserted through the hollow cutting member to extend substantially beyond the distal end of the cutting member and, consequently, beyond the distal end of the guiding catheter. The distal end of the guide wire is advanced up arteries of a patient, through the aortic valve, and into the left ventricle. The guiding catheter is advanced over the guide wire into the left ventricle and positioned near the apex of the left ventricle, and the guide wire is then removed. The foot is then rotated 180° relative to the guiding catheter by manipulation at the actuation handle. The foot is then moved distally relative to the distal end of the guiding catheter and planted (by applying light pressure) on the heart wall adjacent the apex.

The distal end of the guiding catheter is moved relative to the foot and towards the heart wall. The second pressure regulator is then operated to form a vacuum in the suction lumen and cause the guiding catheter to be held against the heart wall. The drilling means is moved distally relative to the distal end of the guiding catheter and entered into the heart wall tissue, thereby drilling a channel in the heart wall. The channel is preferably drilled fifty to sixty five percent of the thickness of the heart wall, and the stop on the actuation handle prevents the cutting member from extending too far into the heart wall. Where a hollow cutting member is used as the drilling means, the cutting member is then twisted (by rotating the proximal end of the cutting member relative to the proximal actuation handle) to detach the cut tissue and the cutting member is withdrawn. The first pressure regulator is then operated to apply a vacuum pulse to move the cut tissue proximally through the cutting member and into a sample collector provided between the cutting member and the first pressure regulator.

The second pressure regulator is operated to release the vacuum in the suction lumen, and the guiding catheter is rotated relative to the control wire to rotate the cutting member relative to the foot and through an arc to a new drilling location where the drilling process is repeated. The drilling is repeated at a number of other relative angles to the foot, e.g., in approximately 15° increments, such that the drilled channels are approximately 0.5 cm to 1 cm apart. Once the desired number of channels are made at a common distance from the foot (through the arc), the actuation handle is operated to move the control wire distally relative to guiding catheter and the drilling process is repeated through a new arc further away from the foot. The process can be repeated through additional arcs further from the foot. Preferably, in total, twenty to fifty channels are drilled.

A second embodiment, similar to the first, is also provided. With the above instruments, a number of advantages are realized. The initial expense of purchasing a mechanical instrument and the expenses for the maintenance thereof are more affordable than the cost and upkeep of laser devices. It will also be appreciated that a mechanical instrument, unlike a laser device, can be disposable. In addition, mechanically drilled channels are free of laser induced thermal damage which is likely to retard both early direct reperfusion and later reperfusion via angiogenesis. Furthermore, the depth of the channels can be controlled mechanically and the myocardial wall is prevented from being perforated. Moreover, the stepping mechanism is relatively easy to manipulate and maneuver.

Additional objects and advantages of the invention will become apparent to those skilled in the art upon reference to the detailed description taken in conjunction with the provided figures.

BRIEF DESCRIPTION OF THE DRAWINGS

FIG. 1 is a top view of a surgical instrument according to the invention;

FIG. 1A is an enlarged cross-section across line 1A—1A in FIG. 1;

FIG. 1B is an enlarged cross-section across line 1B—1B in FIG. 1;

FIG. 2 is a section view through line 2—2 of FIG. 1;

FIG. 3 is a section view through line 3—3 of FIG. 1;

FIG. 4 is a section view through line 4—4 of FIG. 1;

FIG. 5 is view similar to FIG. 2 in which a guide wire extends through a guiding catheter portion of the instrument of the invention;

FIG. 6 is a distal end view of the surgical instrument configured as shown in FIG. 5;

FIG. 7 is a top view of the distal end of the surgical instrument described in FIG. 5;

FIG. 8 is a partial section top view of the distal end of the surgical instrument, similarly configured as in FIG. 7;

FIG. 9 is a view similar to FIG. 2 in which a pressure regulator is coupled to a drilling means extending through guiding catheter;

FIG. 10 is a view similar to FIG. 9 in which the drilling means has been moved relatively distally;

FIG. 11 is a distal end view of the surgical instrument in which the foot has been rotated and the drilling means extends beyond the distal end of the guiding catheter;

FIG. 12 is a partial section top view of the distal end of the surgical instrument, configured as shown in FIG. 11;

DETAILED DESCRIPTION OF THE PREFERRED EMBODIMENTS

Figure 13:
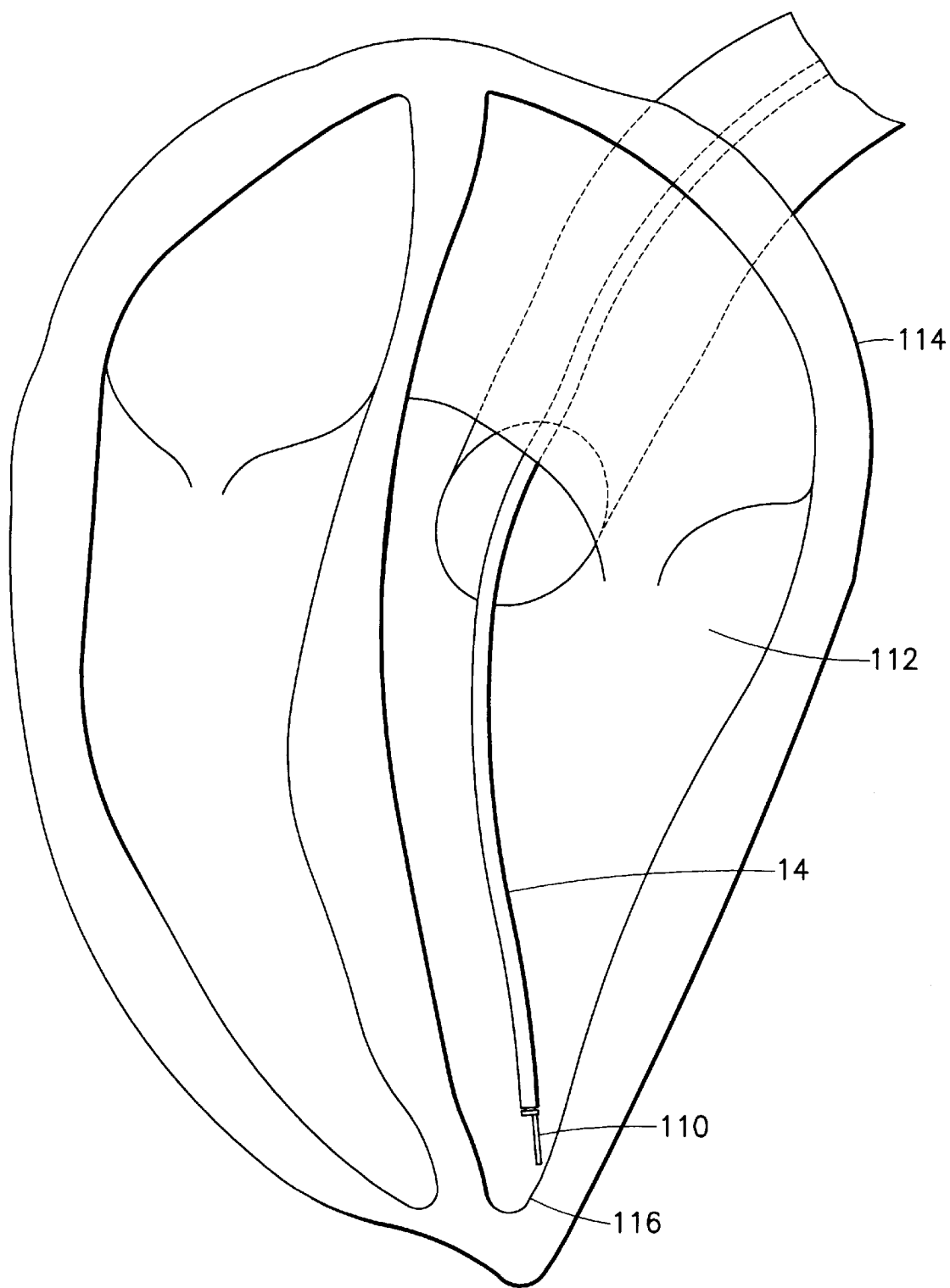
FIGS. 13–22 illustrate the method of the invention.

Turning now to FIGS. 1, 1A, and 1B, a surgical instrument 10 according to the invention is shown. The instrument 10 generally includes a proximal actuation handle 12 and a flexible guiding catheter. The flexible guiding catheter 14 has proximal and distal ends 16, 18, a preferably lubricous channeling lumen 20, a suction lumen 22, and a preferably lubricous control lumen 24. The guiding catheter 14 is preferably approximately 120 cm in length and preferably has a slit opening 26 into the control lumen 24 at its distal end 18. Referring to FIGS. 1 and 2, and as a brief overview to a more detailed description below, a hollow cutting member 28 extends through the channeling lumen 20 and is moveable distally relative to the guiding catheter 14 with a cutting actuation mechanism 30, described below. The cutting member 28 is preferably a section of thin walled hypodermic tubing having a sharpened distal end and is preferably provided with a first proximal connector 32 for coupling the cutting member to a first pressure regulator or vacuum source 29 (indicated in FIG. 9). The first proximal connector 32 or luer connector is preferably provided with longitudinal traction ridges 33. Referring to FIGS. 1 and 4, a flexible control wire 34 extends through the control lumen 24 and is movable distally and rotatably relative to the guiding catheter with a control actuation mechanism 36, described below, on the actuation handle. The control wire is sufficiently flexible to flex and buckle with each contraction of the heart, the importance of this property being described below. The control wire 34, at its distal end located beyond the distal end 18 of the guiding catheter 14, has a reference means or "foot" 38, described further below. Referring to FIGS. 1 and 3, a suction conduit 40 extends into the actuation handle 12 and is coupled to the suction lumen 22 of the guiding catheter 14. The suction conduit has a second proximal connector 42 which is coupled to a second pressure regulator or vacuum source 44 (FIG. 3).

Referring to FIGS. 1 through 4, the actuation handle 12 is generally an elongate plastic molded member having a frustoconical distal end 50, finger grips 52, and a longitudinal throughbore 54. In addition, the handle has a recessed surface 56, a bore 57 located under the distal portion of the recessed surface, and a plurality of lateral slots 58 intersecting the throughbore 54 and the recessed surface 56. Each of the lateral slots 58 preferably has a distally directed barb 59 at its intersection with the throughbore 54. The recessed surface 56 also includes a first vertical slot 60 substantially coaxial with the proximal end of the channeling lumen 20, and a second vertical slot 62 substantially coaxial with the proximal end of the control lumen 24 and oriented orthogonal to the lateral slots 58. A raised divider 64 separates the first and second vertical slots 60, 62. The proximal end of the guiding catheter 14 is sheathed in a collar 66 which is interference fit in the throughbore 54 to couple the guiding catheter to the actuation handle 12.

Referring to FIGS. 1 and 2, the cutting actuation mechanism 30 includes a sliding switch 70 having a base 72 extending into the first vertical slot 60, an external element 74 having knurls 76, a distal projection 78, and a ring 80. The control actuation mechanism 30 also includes a spring 82, which is seated in the bore 57 and extends over the distal projection 78, thereby biasing the sliding switch 70 proximally within the first vertical slot 60. Distal movement of the sliding switch 70 moves the distal projection 78 into the bore 57. The cutting member 28 extends through the ring 80 and is provided with a stationary ring 84, 86 on either side of the cutting member ring 80, such that movement of the sliding switch 70 translates into movement of the cutting member 28. Indicia 88 are provided on the recessed surface 56 to indicate how far the sliding switch has been moved, and to thereby indicate how far the cutting member has been moved. Preferably, the same indicia 88 or other indicia also signifies how far the distal end of the cutting member 28 extends beyond the distal end 18 of the guiding catheter 14.

Referring to FIGS. 1 and 4, the control actuation mechanism 36 includes a radial handle 90 having an external gripping knob 92 and an arm 94 extending through the second vertical slot 62 and coupled to the control wire 34, preferably by a weld 96. Proximal and distal movement of the handle 90 through the second vertical slot operates to move the control wire 34 likewise relative to the guiding catheter 14. Indicia 98 are provided on the recessed surface 56 to indicate the relative movement of the control wire. Additionally, the handle 90 may be rotated through the lateral slots 58 to rotate the control wire 34, and thereby the foot 38, relative to the guiding catheter 14. Indicia 100 are also provided to indicate the degree of relative rotation, preferably in 15° increments. The foot 38 extends preferably orthogonally to the control wire and across the distal end 18 of the guiding catheter. The foot 38 preferably has approximately the surface area of a cross section through the guiding catheter less the area of a cutout 102. The cutout 102 permits a guide wire, described below with respect to the method of the invention, to extend through the foot 38.

Figure 14:
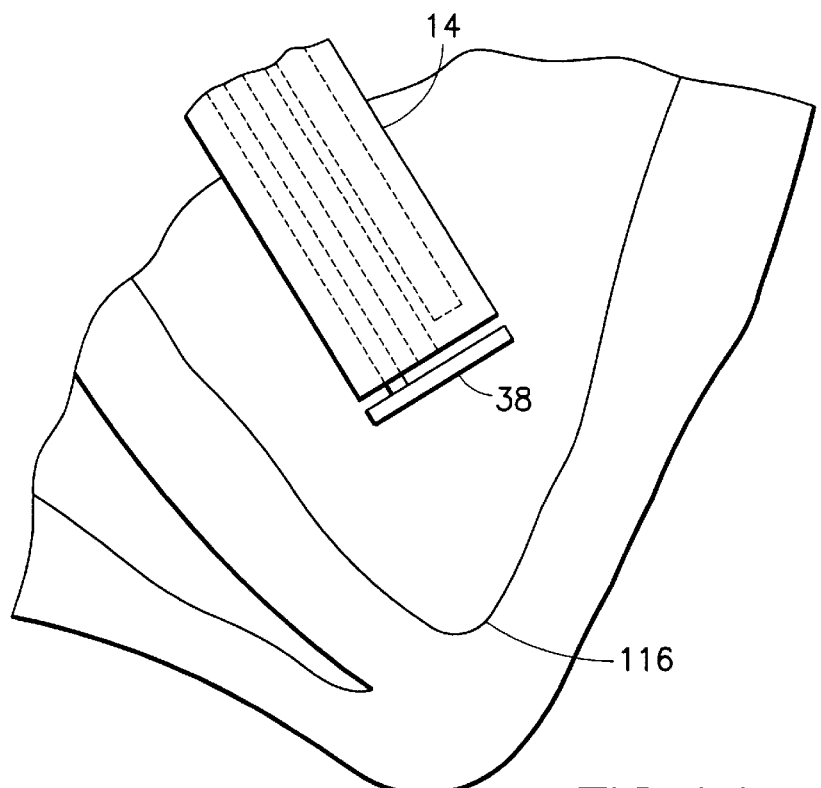
Figure 15:
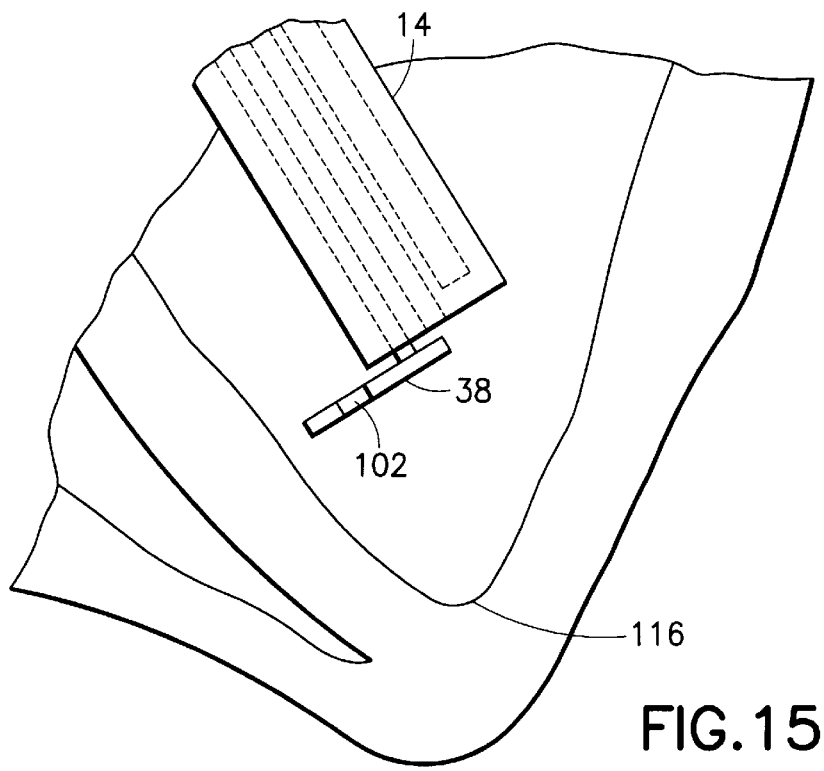

By way of example, the instrument 10 can be used to perform surgery, such as PMR, within the heart. Turning to FIG. 5, a guide wire 110 is inserted through the first proximal connector 32 of the hollow cutting member 28 to extend through and substantially beyond the distal end of the cutting member and, consequently, beyond the distal end 18 of the guiding catheter 14, and through and beyond the cutout 102 of the foot 38, e.g., approximately 180 cm beyond. The femoral artery of patient is then accessed, preferably via a standard Seldinger technique and the guide wire is advanced up the femoral and iliac arteries into the aorta, around the aortic arch, through the aortic valve, and into the left ventricle of the heart of a patient. Turning to FIGS. 6 through 8 and 13, the guiding catheter is then advanced over the guide wire 110 into the left ventricle 112 of the heart 114 and positioned near the apex 116 of the left ventricle. The guide wire 110 is then removed (FIG. 14), and the proximal connector 32 is coupled to the second pressure regulator 29 (FIG. 9).

Figure 16:
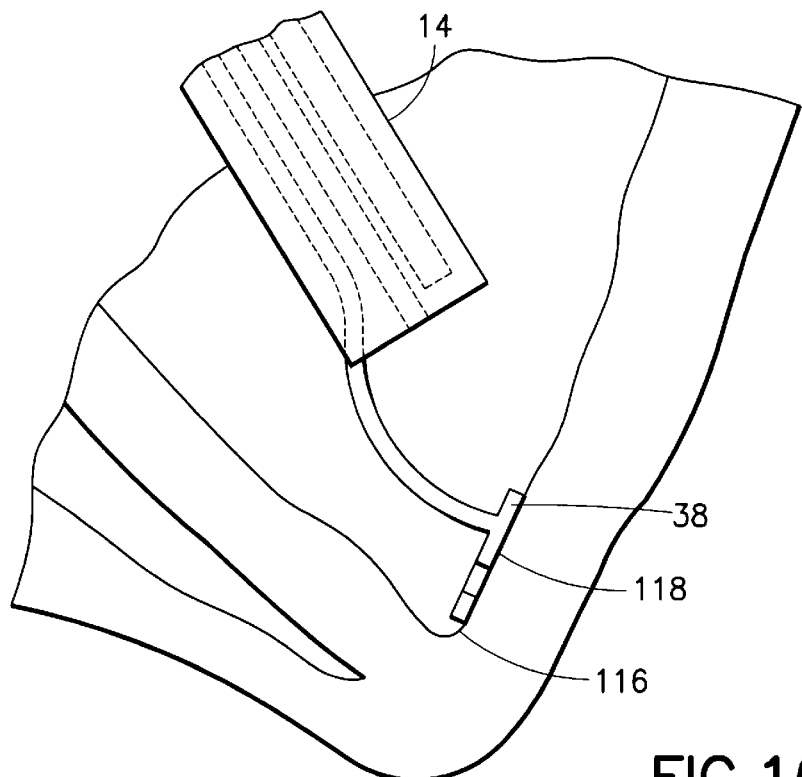

Turning to FIGS. 1, 4, 11, 12 and 15, the control handle 90 (FIG. 4) is preferably then rotated through a first lateral slot 58a (FIG. 1) such that the guiding catheter 14 and the foot 38 are rotated approximately 180° relative to each other. Referring to FIG. 16, the foot 38 is then moved distally relative to the distal end of the guiding catheter and planted by applying light pressure, e.g., a few grams of pressure, on the heart wall 118 adjacent the apex 116. The control wire 34 flexes with each heart contraction and the foot 38 maintains its positioning on the heart wall 118. The flexibility of the control wire and the relatively large surface area of the foot inhibits the foot from puncturing the heart wall 118 during contractions of the beating heart.

Figure 17:
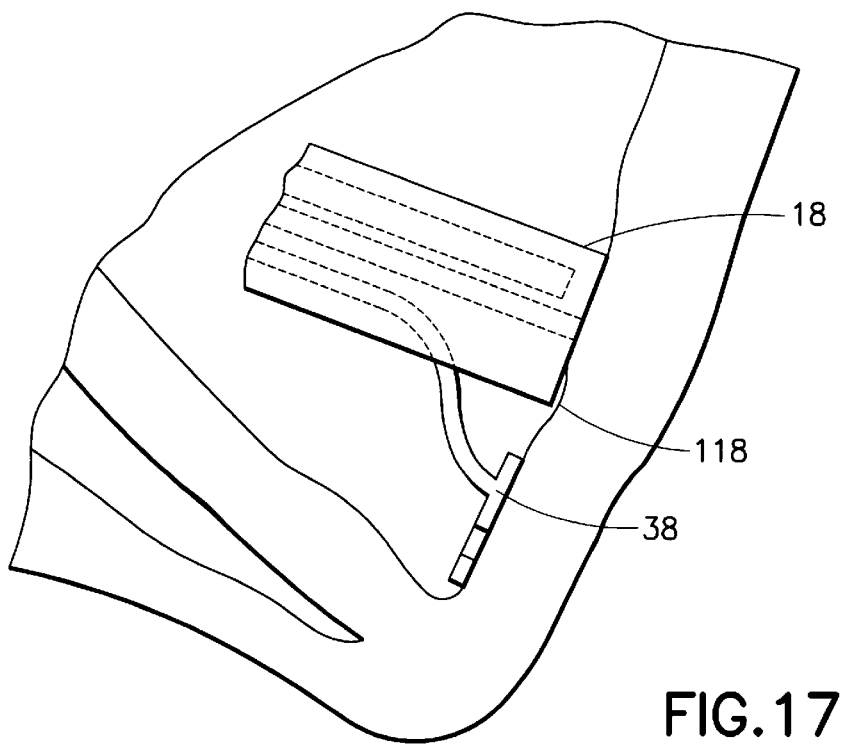

Turning to FIG. 17, the distal end 18 of the guiding catheter 14 is then moved relative to the foot 38 and towards the heart wall 118, such that both the foot and the distal end of the guiding catheter rest on the heart wall. The slit opening 26 permits the control wire 34 to bow or bend out of the side of the distal end of the guiding catheter and therefore permits greater maneuverability of the guiding catheter relative to the foot 38.

Figure 18:
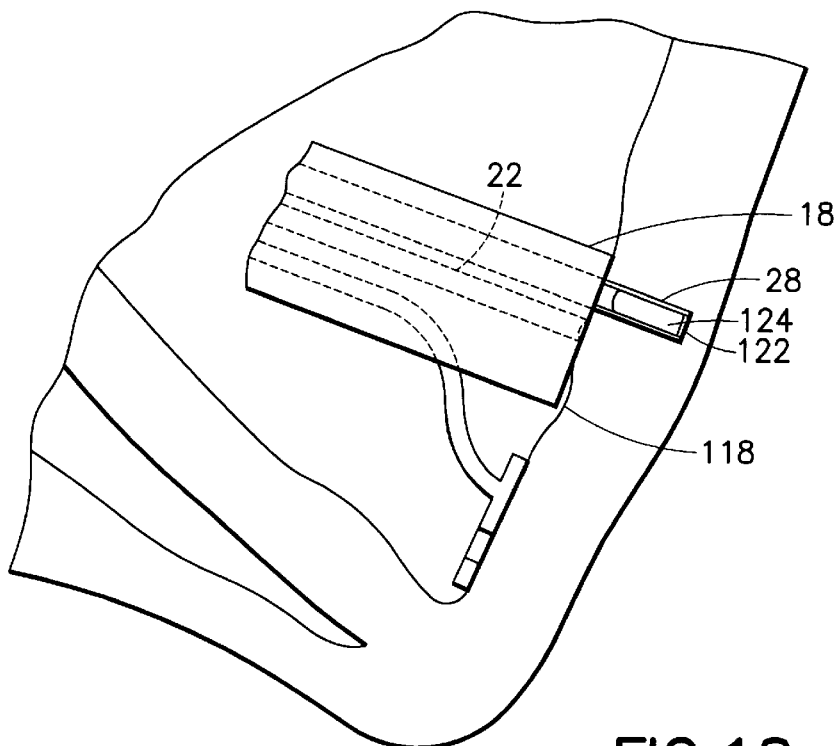

Referring to FIG. 18, the second pressure regulator 44 (FIG. 3) is then operated to form a vacuum in the suction lumen 22 and cause the guiding catheter to be held against the heart wall 118. With the guiding catheter and foot in this position, when the heart beats, the catheter and foot are maintained against the heart wall with the length of the catheter between the heart wall and the handle absorbing the movement. Referring to FIGS. 10 and 18, with the catheter on the heart wall, the cutting member 28 is then moved distally relative to the distal end 18 of the guiding catheter and entered into the heart wall tissue, thereby drilling a channel 122 in the heart wall. The channel 122 is preferably drilled fifty to sixty-five percent of the thickness of the heart wall, and the distal projection 78 on the sliding switch 70 limits the distal movement of the cutting member 28, preventing the cutting member from extending too far into (or even through) the heart wall (FIG. 10). The cutting member 28 is then twisted relative to the guiding catheter by rotating the proximal connector 32 of the cutting member, the traction ridges 33 on the proximal connector 32 being provided to assist the surgeon in the rotation. The twisting action detaches the drilled tissue 124 and the cutting member 28 is then withdrawn.

Figure 19:
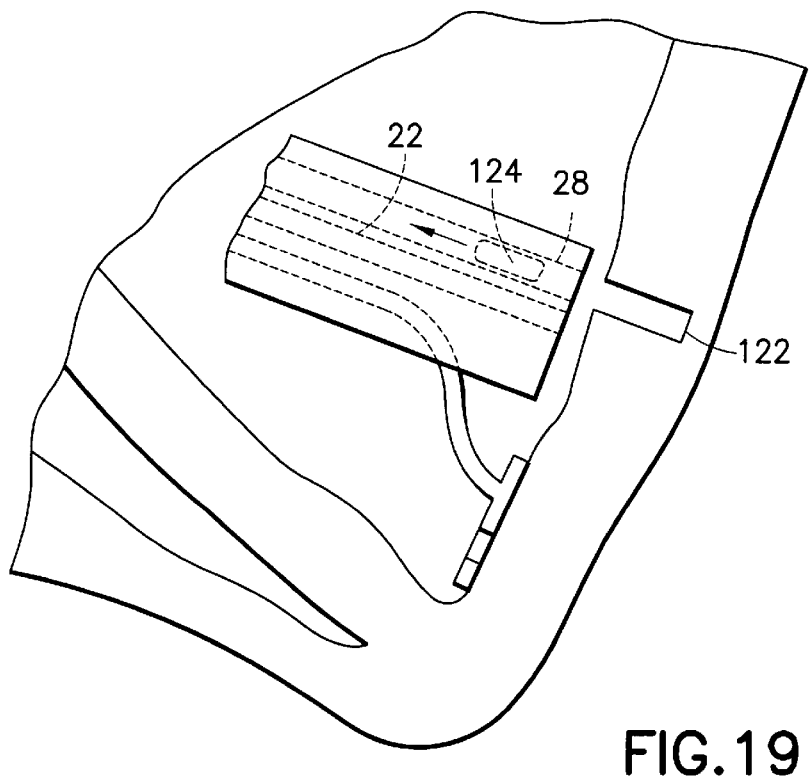

Turning to FIG. 19, the second pressure regulator is operated to release the vacuum in the suction lumen 22 and the first pressure regulator 29 is operated to apply a vacuum pulse to move the cut tissue 124 proximally through the cutting member 28 and into a sample collector (not shown) provided between the cutting member and the first pressure regulator.

Figure 20:
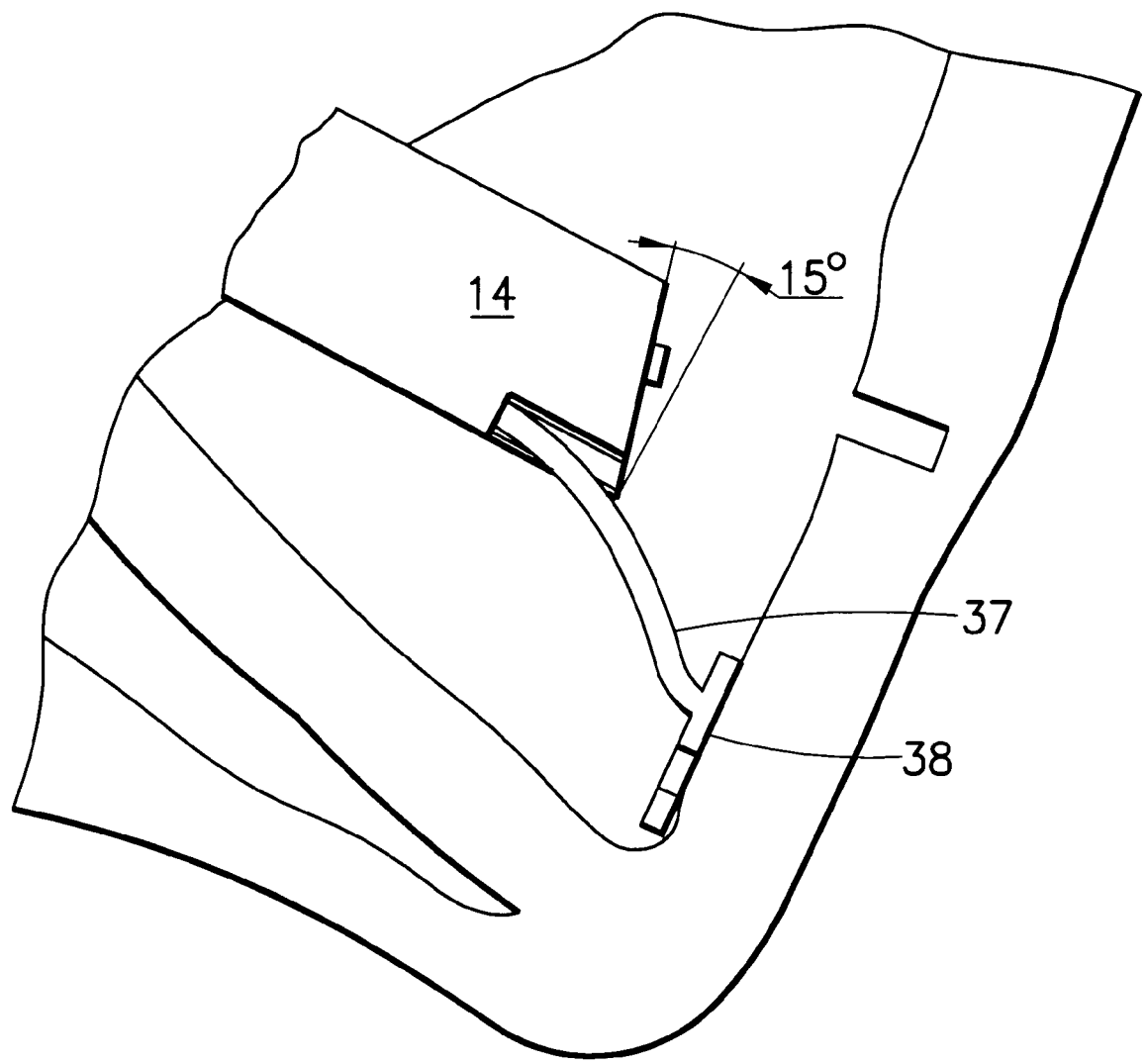

Referring to FIGS. 1 and 20, with the foot 38 planted with a few grams of pressure, the actuation handle 12 and the control handle 90 are rotated preferably approximately 15° relative to each other, with the arm 94 of the control handle moving through the first lateral slot 58a. The degree of rotation is indicated by the indicia 100. The drilling process is then repeated as described above to create another channel in the heart wall. As desired, the distal end 18 of the guiding catheter may be rotated through an arc relative to the control wire and foot to a new drilling location, such that channels are drilled in the heart wall preferably approximately 0.5 cm to 1 cm apart.

Figure 21:
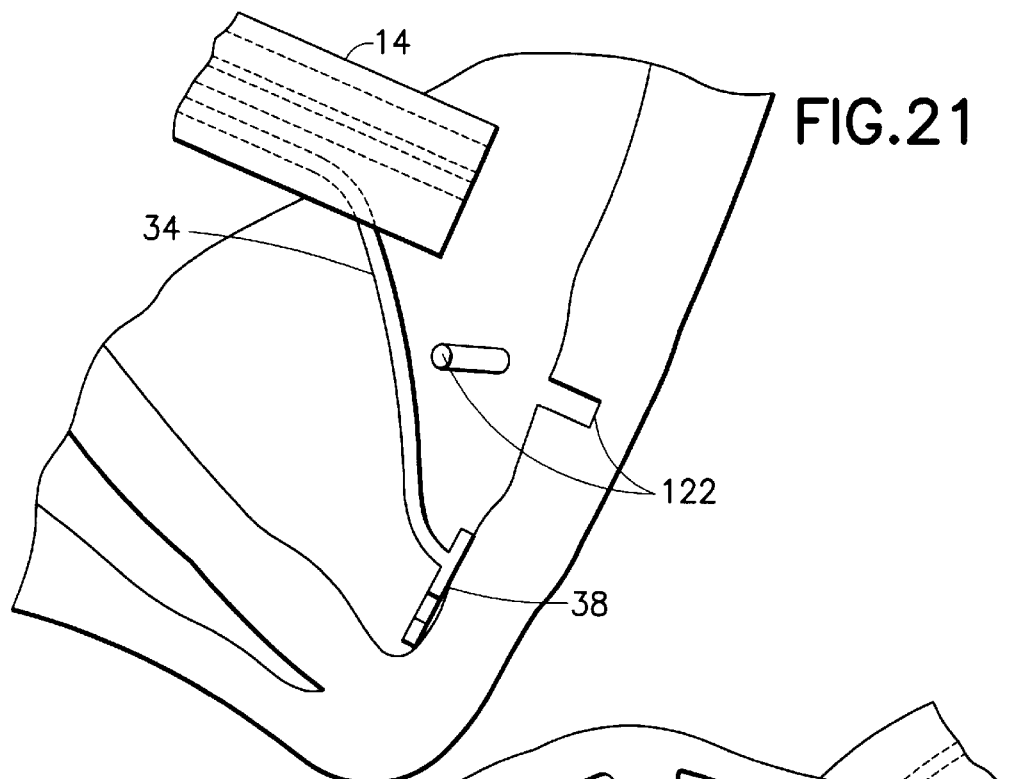
Figure 22:
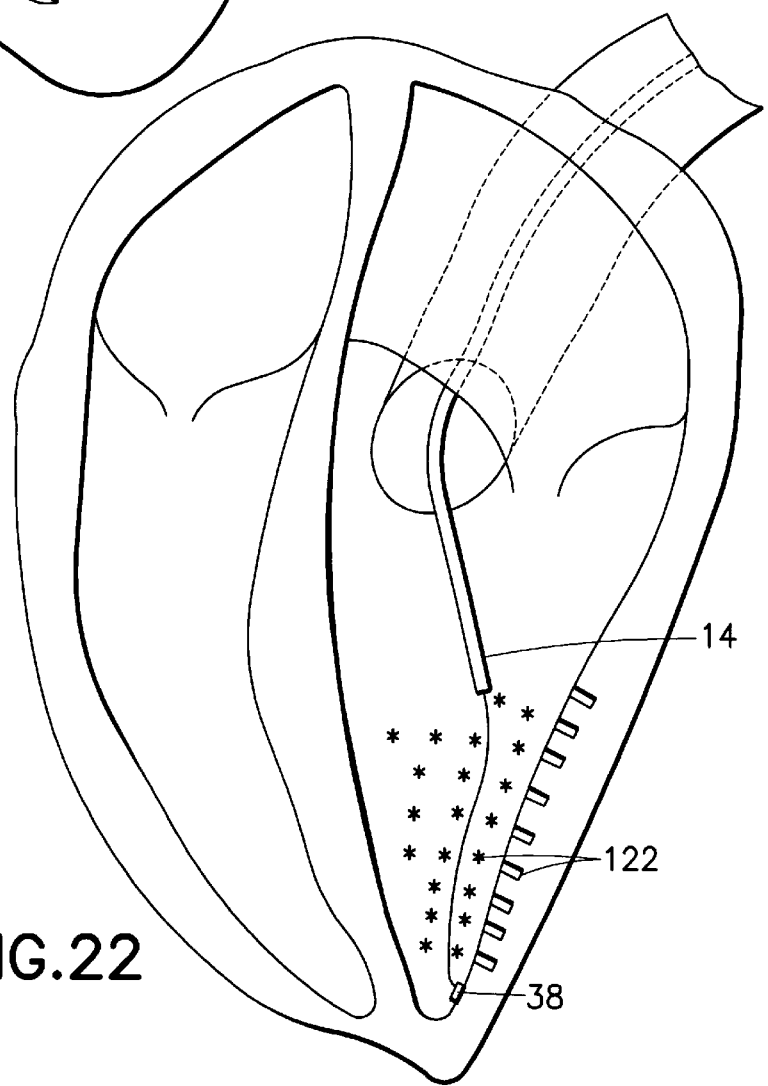

Turning to FIGS. 1 and 21, once the desired number of channels 122 are made at a common distance from the foot 38 (through the arc), the control handle 90 is moved through the second vertical slot 62 and beyond a barb 59 such that the control wire 34 has been moved a selected distance relative to the actuation handle 12 and is prevented by the barb from relative proximal movement unless carefully moved around the barb. It will be appreciated that while, for clarity, the above has been described in terms of movement of the control wire, in actuality the guiding catheter 14 is being moved proximally relative to the foot in the heart chamber. Referring to FIG. 22, the drilling process is then repeated through a new arc further away from the foot 38. The process is repeated until the desired number of channels 122 have been drilled. Preferably, in total, twenty to fifty channels are drilled.

After the desired number of channels have been drilled, the control handle 90 is moved proximally relative to the guiding catheter 14 through the second vertical slot 62 and around the barbs 59 to return the control wire to its initial relative position. The foot 38 is thereby retracted against the distal end 18 of the guiding catheter. Once the foot is retracted, the guiding catheter is withdrawn from the patient.

Figure 23:
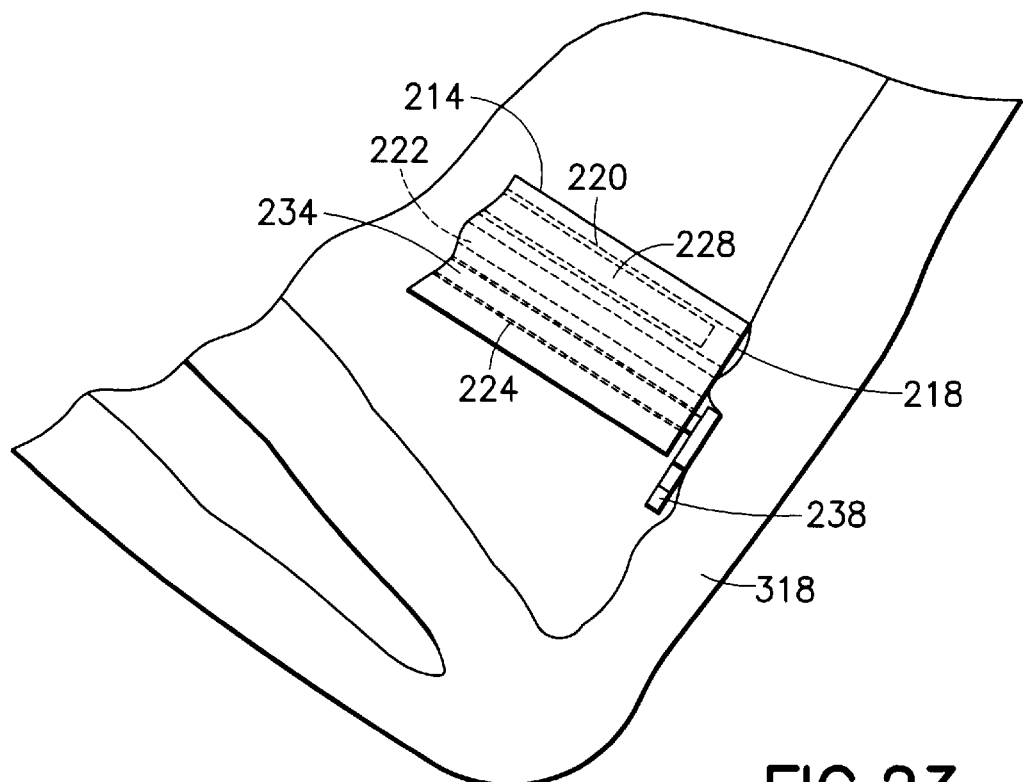
FIGS. 23–26 illustrate second embodiments of the instrument and method of the invention.

Turning now to FIG. 23, a second embodiment of the surgical instrument of the invention, substantially similar to the first embodiment (with like parts incremented by 200), is shown. The instrument generally includes a proximal actuation handle, described above, and a flexible guiding catheter 214. The flexible guiding catheter 214 has a distal end 218, a preferably lubricous channeling lumen 220, a suction lumen 222, and a preferably lubricous control lumen 224. Unlike the first embodiment, the tubular member is preferably not provided with a slit opening into the control lumen. A cutting member 228 extends through the channeling lumen 220 and is actuated via a cutting actuation mechanism as described above with respect to the cutting actuation mechanism 30 of the first embodiment. A control wire 234 having a "foot" 238 at its distal end extends through the control lumen 224 and is actuated via a control actuation mechanism similar to the control actuation mechanism 36 described above.

Figure 24:
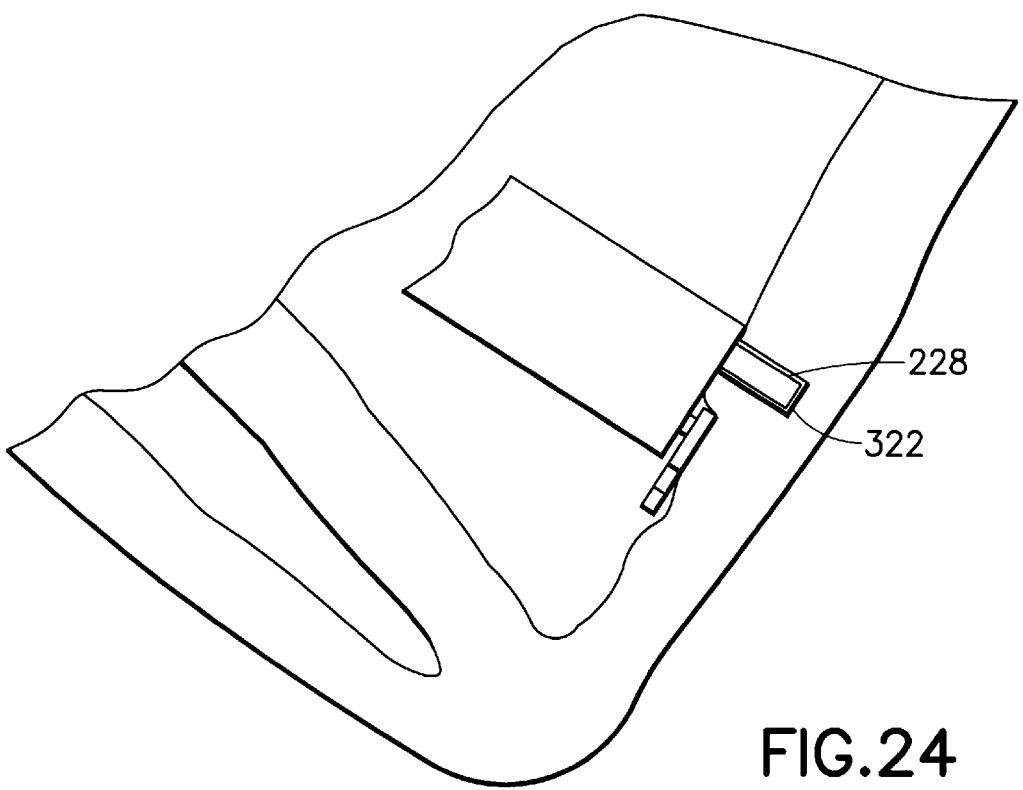
Figure 25:
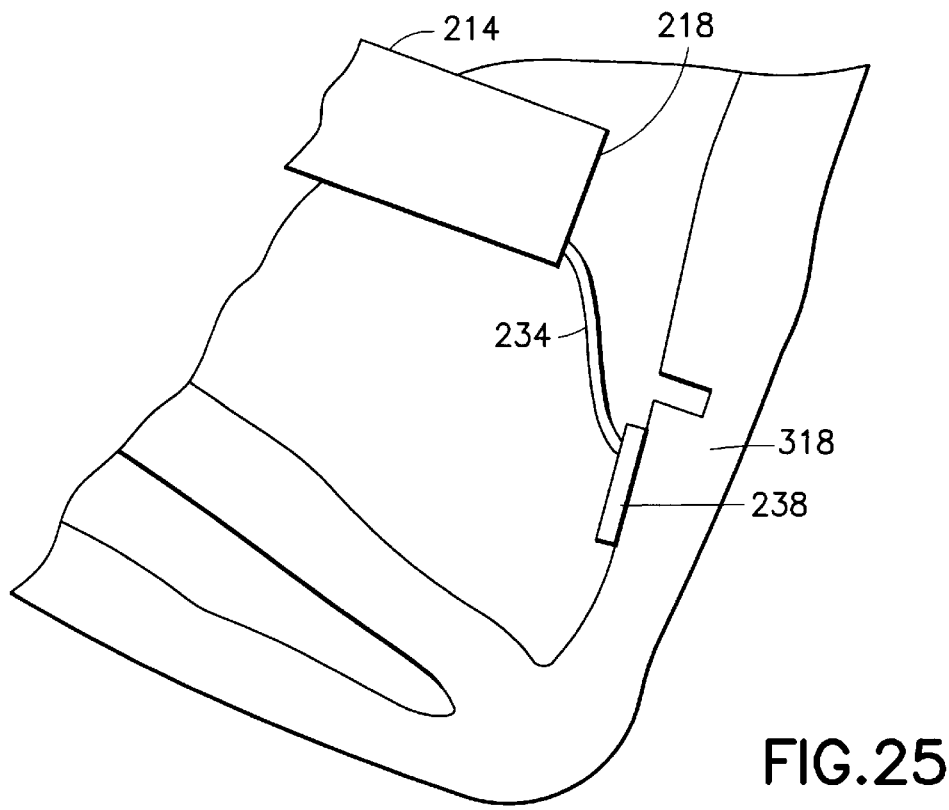
Figure 26:
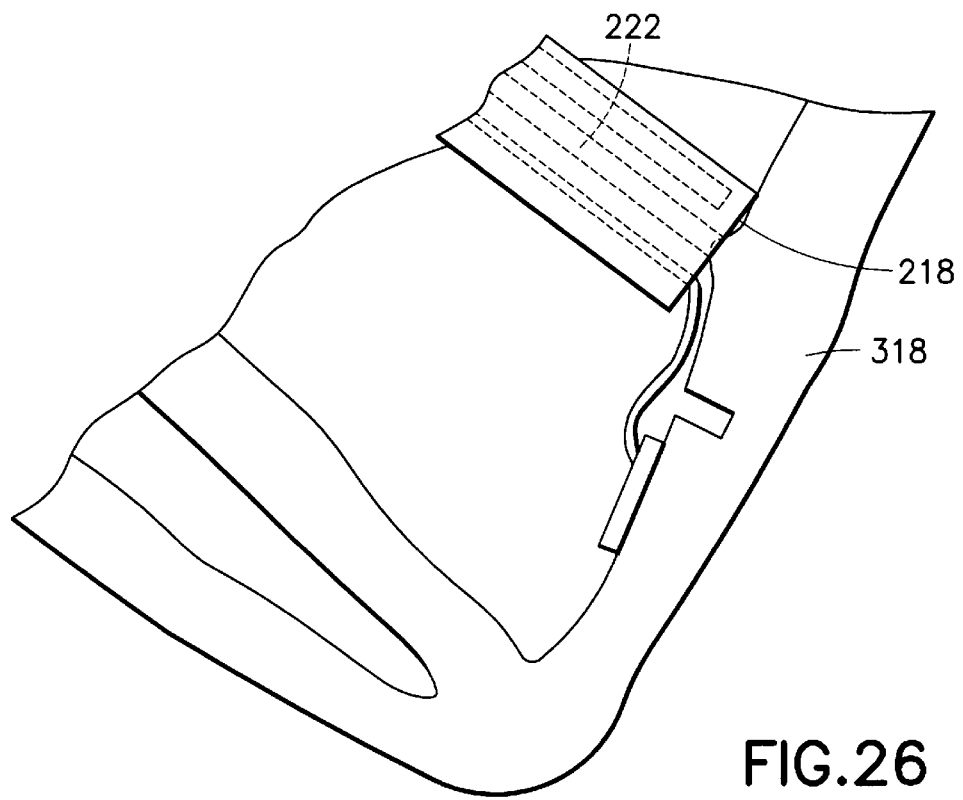

Still referring to FIG. 23, the instrument is advanced into a chamber of the heart over a guide wire and maneuvered adjacent the heart wall 318. Suction is applied through the suction lumen 222 to hold the distal end 218 of the guiding catheter 214 and the foot 238 against the heart wall 318. Turning to FIG. 24, the cutting member 228 is then actuated to drill a channel 322 into the heart wall. Referring to FIG. 25, the suction is released and the control actuation mechanism is operated to move the control wire 234 and the guiding catheter 214 relative to each other such that distal end 218 of the guiding catheter moves proximally relative to the foot 238, with the foot remaining planted on the heart wall 318. Turning now to FIG. 26, the distal end 218 of the guiding catheter is again moved towards the heart wall 318, and suction is applied through the suction lumen 222 to hold the distal end of the guiding catheter against the heart wall. The control actuation mechanism is then operated to retract the control wire 234 into the guiding catheter 214 such that the foot 238 is pulled against the distal end 218 of the guiding catheter, to the position shown in FIG. 23. The cutting member 228 is again actuated to drill a channel in the heart wall. The process is repeated until the desired number of channels have been drilled into the heart wall. Once the desired number of channels have been drilled, the suction in the suction lumen is released and, with the foot abutting the distal end of the guiding catheter, the guiding catheter is withdrawn from the patient.

With the above instruments, a number of advantages are realized. The initial expense of purchasing a mechanical instrument and the expenses for the maintenance thereof are more affordable than the cost and upkeep of laser devices. It will also be appreciated that a mechanical instrument, unlike a laser device, can be disposable. In addition, drilled channels are free of laser induced thermal damage which is likely to retard both early direct reperfusion and later reperfusion via angiogenesis. Furthermore, the depth of the channels can be controlled mechanically and the myocardial wall is prevented from being perforated. Moreover, the stepping mechanism is relatively easy to manipulate and maneuver.

There have been described and illustrated herein several embodiments of a instrument and a method of performing PMR. While particular embodiments of the invention have been described, it is not intended that the invention be limited thereto, as it is intended that the invention be as broad in scope as the art will allow and that the specification be read likewise. Thus, while particular relative dimensions have been shown in the drawings, it will be appreciated that other relative dimensions may be used. In particular, the dimensions of the guiding catheter, the cutting member, the foot, and the guide wire are preferably smaller than shown relative to the actuation handle, being shown larger in the drawings for the purpose of clarity. Furthermore while the drilling means has been described as a cutting member, it will be appreciated that other drilling means may be used with the instrument. For example, in place of the cutting member, a conventional laser or a cryogenic needle as disclosed in co-owned U.S. Ser. No. 08/918,032, filed on Aug. 25, 1997, and entitled "Cryogenic Catheter System And A Method Of Cryogenically Inducing Percutaneous Myocardial Revascularization Using The Same", may be used. In addition, other effecting means in place of a drilling means, e.g., clamps and forceps, can also be used with the instrument. Also, while the use of the instrument has been described in a procedure within the left ventricle of the heart, it will be recognized that the instrument may be used in both ventricles and both atria. Moreover, while particular configurations have been disclosed in reference to the cutting actuation mechanism and the control actuation mechanism, it will be appreciated that other configurations could be used as well, especially configurations designed to move the cutting member and the control member incrementally relative to the actuation handle. For example, a ratchet and pawl assembly, as disclosed in U.S. Pat. No. 5,281,197, can be used. Furthermore, while the foot has been described with respect to one shape, it will be understood that any shape advanceable into the heart and having sufficient surface area to prevent the foot from puncturing the heart wall can be similarly used. The foot can also be provided with suction capability by using hypotubing coupled to a pressure regulator instead of wire 34. In addition, while first and second pressure regulators are described, it will be appreciated that the first and second pressure regulators may be separate pumps or may be separate valves coupled to a single pump. It will therefore be appreciated by those skilled in the art that yet other modifications could be made to the provided invention without deviating from its spirit and scope as so claimed.

What is claimed is:

1. A surgical instrument for use in a beating heart and movable with respect to a location on a heart wall of the heart, comprising:
   a) a flexible tubular member having a distal end, a proximal end, and a first lumen;
   b) an effecting means for operating on the heart provided at said distal end of said tubular member;
   c) a flexible control member extending through said first lumen and having a proximal end and a reference means at a distal end; and
   d) means for moving said control member relative to said tubular member,
wherein said reference means is plantable on the location on the heart wall such that when said control member is moved relative to said tubular member, said effecting means can be moved non-axially relative to the location.

2. A surgical instrument according to claim 1, wherein: said effecting means is a drilling means.

3. A surgical instrument according to claim 2, wherein: said drilling means is a mechanical cutting means.

4. A surgical instrument according to claim 1, wherein: said reference means is a foot member having a relatively large surface area contactable with the heart wall.

5. A surgical instrument according to claim 4, wherein: said tubular member has a cross-sectional area and said foot has a surface area substantially equal to said cross-sectional area less a cutout area.

6. A surgical instrument according to claim 1, wherein: said tubular member is provided with a second lumen and said effecting means is movable through said second lumen.

7. A surgical instrument according to claim 1, wherein: said tubular member is provided with a third lumen, said third lumen being coupled to a pressure regulating means.

8. A surgical instrument according to claim 1, wherein: said means for moving said control member relative to said tubular member is for moving said control member distally in a stepwise manner relative to said tubular member.

9. A surgical instrument according to claim 1, wherein: said means for moving said control member relative to said tubular member moves said control member proximally, distally, and rotatably relative to said tubular member.

10. A surgical instrument according to claim 1, further comprising:
    e) an actuation handle housing said means for moving said control member, said actuation handle provided with first indicating means for indicating a distance said control member has been moved relative to said tubular member.

11. A surgical instrument according to claim 10, wherein: said actuation handle is provided with second indicating means for indicating a rotational movement of said control member relative to said tubular member.

12. A surgical instrument according claim 1, wherein: said distal end of said tubular member defines a slit opening into said first lumen.

13. A surgical instrument for use in a beating heart and movable with respect to a location on a heart wall of the heart, comprising:
    a) a flexible tubular member having a distal end, a proximal end, a control lumen, and a channeling lumen;
    b) an actuation handle having a bore, said proximal end of said tubular member being coupled to said bore;
    c) a drilling means for forming a channel in the heart wall, said drilling means extending through said channeling lumen;
    d) a control member extending through said control lumen and having a reference means located at a distal end for locating said surgical instrument; and
    e) a control actuation means coupled to said actuation handle for moving said control wire relative to said tubular member,
wherein said reference means is plantable on the location on the heart wall such that when said control actuation means is operated to move said control wire relative to said tubular member, said drilling non-axially means is movable relative to the location.

14. A surgical instrument according to claim 13, further comprising:
    f) a drilling actuation means coupled to said actuation handle for moving said drilling means proximally and distally relative to said tubular member.

15. A surgical instrument according to claim 14, wherein: said drilling actuation means includes a limiting means for limiting a distance said drilling means may be moved relative to said tubular member.

16. A surgical instrument according to claim 14, wherein: said actuation handle includes indicating means for indicating a distance said drilling means has been moved relative to said tubular member.

17. A surgical instrument according to claim 14, wherein: said drilling means is rotatable relative to said tubular member.

18. A surgical instrument according to claim 13, wherein:

said drilling means has a hollow portion.

19. A surgical instrument according to claim 18, wherein:

said drilling means comprises a section of hypodermic tubing.

20. A surgical instrument according to claim 19, wherein:

said hypodermic tubing has a sharpened distal end.

21. A surgical instrument according to claim 18, further comprising:

f) a first connecting means for coupling said drilling means to a first pressure regulator.

22. A surgical instrument according to claim 13, wherein:

said tubular member is provided with a suction lumen and said suction lumen is coupled to a second connecting means for coupling said suction lumen to a second pressure regulator.

23. A method of performing a surgical procedure on an inner heart beating wall in a chamber of a heart with an instrument having a flexible tubular member with a distal end, a proximal end, and a first lumen, an effecting means for operating on the heart wall provided at the distal end of the tubular member, a flexible control member extending through the first lumen and having a proximal end and a reference means for locating the instrument at a distal end, said method comprising:

a) inserting the distal end of the tubular member into the chamber of the heart;

b) moving the control member relative to the tubular member such that the reference means is positioned on the heart wall;

c) operating the effecting means to perform the surgical procedure;

d) moving the control member relative to the tubular member such that the distal end of the tubular member is non-axially movable relative to the reference means; and e) repeating steps c) and d), at a plurality of locations along the heart wall.

24. A method according to claim 23, further comprising:

f) after said step of moving the control wire relatively distally, placing the distal end of the tubular member against the heart wall; and g) after said step of operating the effecting means, removing the distal end of the tubular member from the heart wall.

25. A method according to claim 23, further comprising:

f) before the step of inserting the tubular member, inserting a guide wire into the chamber of the heart, wherein the step of inserting the tubular member comprises advancing the tubular member over the guide wire; and g) after said step of inserting the tubular member, removing the guide wire.

26. A method according to claim 23, wherein:

the reference means is a foot member having a relatively large surface area, and the effecting means is a drilling means.

27. A method according to claim 26, wherein:

said step of moving the control member comprises rotating the control member relative to the tubular member and moving the control member axially relative to the tubular member.

28. A method according to claim 26, wherein:

said step of moving the control member comprises moving the control member in a stepwise manner.

29. A method according to claim 26, wherein:

the tubular member has a channeling lumen through which the drilling means extends, and said step of operating the effecting means comprises inserting the drilling means into the heart wall.

30. A method according to claim 29, wherein:

the drilling means is inserted approximately fifty to sixty-five percent into the heart wall.

31. A method according to claim 26, wherein:

the tubular member has a suction lumen which is coupled to a pressure regulator means for providing a vacuum through the suction lumen, and said step of operating the effecting means comprises moving the tubular member against the heart wall, applying suction through the suction lumen to hold the tubular member against the heart wall, and drilling a channel in the heart wall with the drilling means.

32. A method according to claim 31, wherein:

the tubular member has a channeling lumen through which the drilling means extends, and said step of operating the effecting means comprises inserting the drilling means into the heart wall.

33. A method according to claim 32, wherein:

the drilling means is rotatable within the channeling lumen and has a hollow portion, and said step of operating the effecting means further comprises rotating the drilling means to drill a channel in the heart wall.

34. A method according to claim 33, wherein:

the drilling means includes a hollow member and is coupled at a proximal end to a pressure regulator means for providing a vacuum through the drilling means, and said step of operating the effecting means further comprises applying suction through the drilling means to remove a cut section of heart tissue from a distal end of the drilling means.

* * * * *